United States Patent [19]

Bahar et al.

[11] Patent Number: 4,868,108

[45] Date of Patent: Sep. 19, 1989

[54] MULTIPLE-ANTIBODY DETECTION OF ANTIGEN

[75] Inventors: Izak Bahar, Chestnut Hill; Francis Cole, Stow, both of Mass.

[73] Assignee: Hygeia Sciences, Incorporated, Newton, Mass.

[21] Appl. No.: 807,930

[22] Filed: Dec. 12, 1985

[51] Int. Cl.$^4$ ............... G01N 33/537; G01N 33/558; G01N 1/48; C12Q 1/00

[52] U.S. Cl. ............................ 435/7; 435/4; 435/14; 435/28; 435/810; 436/514; 436/535; 436/536; 436/808; 422/56; 422/60; 422/61

[58] Field of Search ............... 435/4, 7, 14, 28, 805, 435/810; 436/514, 535, 536, 808, 809, 810; 422/56, 60, 61

[56] References Cited

U.S. PATENT DOCUMENTS

| | | | |
|---|---|---|---|
| 3,791,932 | 2/1974 | Schuurs et al. | 195/103.5 |
| 3,888,629 | 6/1975 | Bagshawe | 23/230 B |
| 4,017,597 | 4/1977 | Reynolds | 424/1.5 |
| 4,094,647 | 6/1978 | Deutsch et al. | 435/7 |
| 4,115,535 | 9/1978 | Giaever | 424/1 |
| 4,157,280 | 6/1979 | Halpert et al. | 195/127 |
| 4,169,012 | 9/1979 | Dawson et al. | 435/7 |
| 4,188,371 | 2/1980 | Weetall | 424/1 |
| 4,200,690 | 4/1980 | Root et al. | 435/7 |
| 4,206,200 | 6/1980 | Guthohrlein et al. | 424/92 |
| 4,248,965 | 2/1981 | Mochida et al. | 435/7 |
| 4,256,833 | 3/1981 | Ali et al. | 435/7 |
| 4,258,001 | 3/1981 | Pierce et al. | 435/7 |
| 4,273,868 | 6/1981 | Walter | 435/14 |
| 4,280,816 | 7/1981 | Elahi | 23/230 |
| 4,287,300 | 9/1981 | Gibbons et al. | 435/5 |
| 4,299,916 | 11/1981 | Litman et al. | 435/6 |
| 4,340,395 | 7/1982 | Magers et al. | 23/230 B |
| 4,343,896 | 8/1982 | Wolters et al. | 435/7 |
| 4,361,648 | 11/1982 | Shuenn-tzong | 435/10 |
| 4,366,241 | 12/1982 | Tom et al. | 435/7 |
| 4,376,110 | 3/1983 | David et al. | 436/513 |
| 4,385,114 | 5/1983 | Guthlein et al. | 435/28 |
| 4,386,224 | 5/1983 | Deetman | 568/703 |
| 4,391,904 | 7/1983 | Litman et al. | 435/7 |
| 4,407,943 | 10/1983 | Cole et al. | 435/7 |
| 4,444,879 | 4/1984 | Foster et al. | 435/7 |
| 4,446,232 | 5/1984 | Liotta | 422/56 |
| 4,448,882 | 5/1984 | Brodbeck et al. | 435/188 |
| 4,457,916 | 7/1984 | Hayashi et al. | 424/101 |
| 4,458,014 | 7/1984 | Ebersole | 435/7 |
| 4,459,358 | 6/1984 | Berke | 435/805 |
| 4,459,359 | 7/1984 | Neurath | 436/507 |
| 4,486,530 | 12/1984 | David et al. | 435/7 |
| 4,503,143 | 3/1985 | Gerber et al. | 435/7 |
| 4,525,452 | 6/1985 | Jones et al. | 435/7 |
| 4,540,659 | 9/1985 | Litman et al. | 435/7 |
| 4,615,972 | 10/1986 | Gallacher | 435/28 |
| 4,632,901 | 12/1986 | Valkirs et al. | 435/5 |
| 4,659,666 | 4/1987 | May et al. | 435/188 |
| 4,681,782 | 7/1987 | Ozkan | 428/36 |
| 4,727,019 | 2/1988 | Valkirs et al. | 435/5 |

FOREIGN PATENT DOCUMENTS

| | | |
|---|---|---|
| 42755 | 12/1981 | European Pat. Off. |
| 56-27654 | 3/1981 | Japan |
| 8001972 | 11/1981 | Netherlands |
| 1464359 | 2/1977 | United Kingdom |
| 2062224 | 5/1981 | United Kingdom |
| 2111676 | 7/1983 | United Kingdom |

OTHER PUBLICATIONS

E. S. Bos et al., "3,3',5,5'-Tetramethylbenzidine As An Ames Test Negative Chromogen for Horse-Radish Peroxidase in Enzyme-Immunoassay", *J. of Immunoassay*, 2(3&4), pp. 187-204 (1981).

P. Nakane, "Preparation and Standardization of Enzyme-Labeled Conjugates", *Immunoassays in the Clinical Laboratory*, Alan R. Liss, Inc., pp. 81-87 (1979).

E. Engvall, "Immunochemical Techniques", in *Methods in Enzymlogy, Part A*, H. V. Vunakis et al., eds. Academic Press, New York, pp. 430-432 (1980).

P. K. Nakane et al., "Peroxidase-labeled Antibody a New Method of Conjugation", J. of Histochemistry and Cytochemistry, vol. 22, pp. 1084-1091 (1974).

M. Uotila et al., "Two-Site Sandwich Enzyme Immunoassay with Monoclonal Antibodies to Human Alpha Fetoprotein", J. Immunological Methods 42, pp. 11-15 (1981).

Primary Examiner—Robert J. Warden
Assistant Examiner—Janelle Graeter
Attorney, Agent, or Firm—John P. Kirby, Jr.; Gary S. Winer; Margaret A. Pierri

[57] ABSTRACT

An assay employing two antibodies. A microporous carrier supports a plurality of layers, in which conjugates form between test antigens and antibodies. Quantitative results are obtained from an immobilized antibody within an indicating substrate.

18 Claims, 3 Drawing Sheets

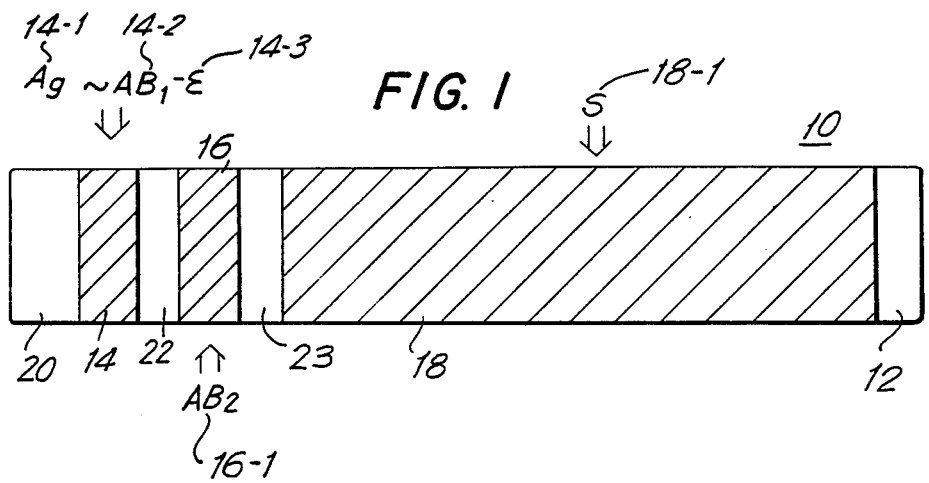
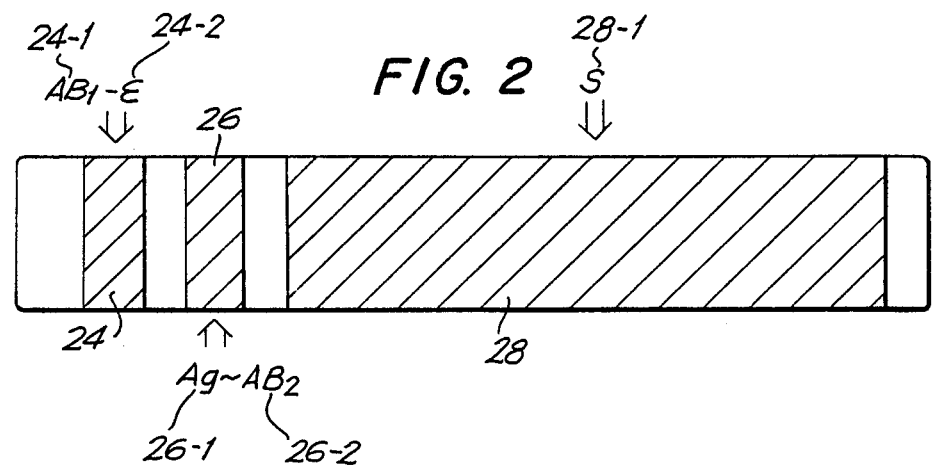
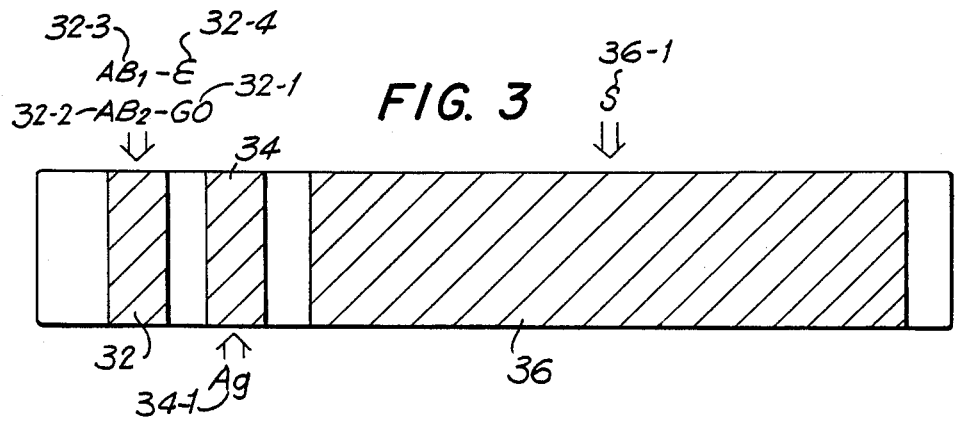

MULTIPLE-ANTIBODY DETECTION OF ANTIGEN

BACKGROUND

The invention relates to enzyme immunoassays, and more particularly to self-contained, one-step assays.

Immunoassays for the detection of antigens are used extensively throughout the world in clinical and medical applications. Common uses include indication of pregnancy and ovulation, and infectious disease. Historically, these assays have been performed by skilled laboratory technicians, entailing the use of numerous reagents in a complicated sequence of steps. Recently, great efforts have been directed towards developing assays which are simpler, less expensive, and more reliable. For example, assay devices now exist which can be used by non-skilled individuals, in non-laboratory environments. These devices, however, are greatly in need of improvement. Problems include complicated steps, difficult interpretation, limited storage life, and unreliability.

One such assay is disclosed in U.S. Pat. No. 4,446,232 to Liotta. The assay therein disclosed has three layers: a first containing an enzyme labelled antibody specific to the test antigen; a second containing bound purified antigen of the type tested for; and a third containing a substrate which reacts with an enzyme bonded to the antibody. This assay suffers from the disadvantage of requiring high antigen purity. Most commonly used antigens, for example HCG, are quite costly to obtain and purify in high quantity. The result is a high cost of manufacture, and a correspondingly high cost to the consumer.

An additional disadvantage of the '232 assay is that both monovalent binding sites on the antibody must be antigen linked for a positive reading. Accordingly, accurate readings require high antigen concentrations, whereby the assay has a low sensitivity.

Moreover, all antigen-linked antibody, and correspondingly all enzyme, diffuses throughout a substrate region, whereby a faint color reaction results. Thus, results are difficult to interpret, and do not provide quantitative information.

It is therefore an object of the invention to provide a single-step enzyme linked immunoassay device which can be easily carried out by a non-skilled user.

It is a further object to provide for higher sensitivity than heretofore known.

It is an additional object to provide for reduced device cost, by employing easily purified, low cost components.

It is yet another object of the invention to provide for sharp, easily readable color indication, while rendering clear quantitative information.

SUMMARY

In accomplishing the foregoing and related objects, the invention provides a unitary assay for indicating the presence of a test antigen in solution. A bibulous microporous support has a plurality of distinct regions, upon which the assay reagents are arranged and dried.

Assays in accordance with the invention include two antibodies, which can be like, depending upon the test antigen. In several embodiments, the antibodies are in separate regions, wherein one antibody is immobilized. The mobile antibody is bonded to an enzyme, which reacts with a substrate in a separate region to yield an indication of test antigen.

In one embodiment, test antigen bonds to the enzyme linked, mobile antibody. Conjugate thus formed next flows to the region containing bound antibody, forming an immobilized conjugate. Accordingly, the enzyme does not reach the substrate region, whereby the presence of test antigen is indicated.

In other embodiments in accordance with the invention, an antigen is immunologically bonded to either the mobile or immobile antibody. In the presence of test antigen, competition arises for binding sites on the unconjugated antibody. Accordingly, enzyme linked antibodies do not become bonded via antigen to immobilized antibody. The enzyme is thus free to reach the substrate region, whereby test antigen is indicated.

In another embodiment, antibody linked with enzyme and antigen are mobile. A second antibody is immobilized within the substrate region. The higher the test antigen level, the greater the quantitative reaction in the substrate region, as conjugate cannot advance through the substrate region after test antigen is exhausted.

In yet another embodiment, one antibody is bonded to enzyme, and another antibody is bonded to glucose oxidase, each mobile within one region. Another region contains immobilized antigen. In the presence of test antigen, conjugates are formed with the antibodies, blocking binding sites against the immobilized antigen. In the substrate region, glucose reacts with glucose oxidase and oxygen to form hydrogen peroxide, a reagent in the indication reaction. In other embodiments, glucose oxidase can be bonded to the freely mobile antibody, to react with glucose in a like manner.

The regions may be located on the carrier in a variety of configurations, provided that the mobile elements pass through the region containing immobilized elements prior to reaching the substrate region. An exception, however, exists in the above described embodiment where antibody is immobilized within the substrate region itself. Examples of configurations include the strip form, having regions of consecutive transverse layers, concentric rings, or superimposed layers.

BRIEF DESCRIPTION OF THE DRAWINGS

Other aspects of the invention will become apparent after considering several illustrative embodiments taken in conjunction with the accompanying drawings, in which:

FIGS. 1-6 are schematic representations of assay devices in accordance with the invention.

DETAILED DESCRIPTION

Figure 4:
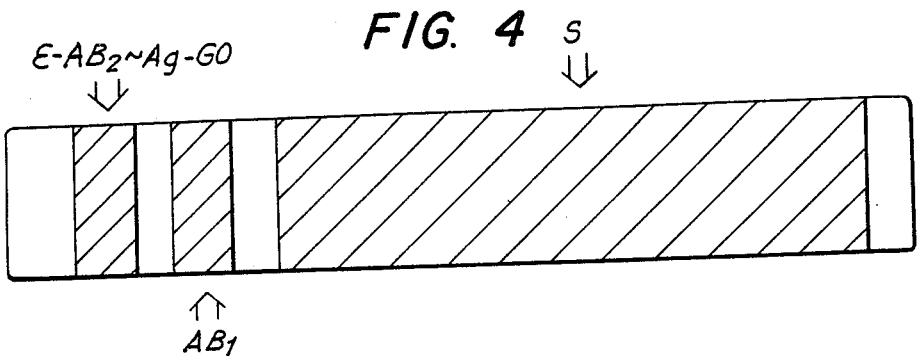

Referring to the Figures, an assay device 10 in accordance with the invention includes a microporous base strip 12 having a pore size preferably less than 25 microns, typically between 5 and 10 microns. Strip 12 is of a bibulous material, for example nylon, or a cellulosic material. Different types of such material may be fastened together to form strip 12, depending on the contents of a given region, as described further below.

In FIG. 1, a first region 14 is coated with a suspension containing antigen 14-1 immunologically bonded to an antibody 14-2, the latter in turn bonded to an enzyme 14-3.

A second region 16 is coated with a suspension containing an antibody 16-1 specific to the antigen tested for. Antibody 16-1 is immobilized within region 16, such that the antibodies will not migrate upon the addition of liquid. Strip 12 material is selected in light of this requirement.

A third region 18 contains a substrate 18-1 which functions as an indicator in the presence of enzyme 14-3.

The strip is air dried or lyophilized after regions 14, 16, 18 are applied, for stabilization.

Device 10 is activated by applying an aqueous test solution to region 20 at the end of strip 12. As the test solution moves through strip 12, conjugate 14-1/14-2/14-3 is reconstituted, whereby same migrates to region 16 with the test solution, passing across buffer region 22. In region 16, competition arises between antigen 14-1 and antigen in the test solution for binding sites on antibody 16-1. As binding sites are occupied by test antigen, conjugate 14-1/14-2/14-3 is free to pass through buffer region 23 to region 18, whereby enzyme 14-3 can participate in the appropriate reactions with substrate 18-1 to indicate antigen presence. Should the test solution not contain the antigen tested for, conjugate 14-1/14-2/14-3 becomes bonded to immobilized antibody 16-1, whereby enzyme 14-3 does not reach region 18. Accordingly, no indication of antigen presence occurs.

Where antigen 14-1 is multideterminant (having at least two identical epitopes (binding sites)), antibodies 14-2 and 16-1 may be the same. Contrarily, where antigen 14-1 is multiepitopic (having at least two different epitopes), antibodies 14-2 and 16-1 may have to be different. Antigen 14-1 need not be the same antigen as that tested for, provided it bonds to antibody 16-1, and blocks bonding of the tested antigen thereto. Moreover, antigen 14-1 need not be pure, provided a sufficient amount of appropriate antigen is present. Nonetheless, antigen 14-1 is obtained in high pure quantities through selection by antibody 14-2. Antibody 14-2, however, must be pure to avoid the migration of enzyme 14-3 to region 18. Accordingly, a monoclonal antibody is preferred, although affinity purified polyclonal antibodies may be used, or affinity purified antibody to antigen 14-1. Bond 24 must be sufficiently strong to withstand the test conditions, whereby an insignificant amount of conjugate 14-2/14-3 freely migrates to region 18.

Referring to FIG. 2, a strip as in FIG. 1 contains three regions 24, 26, 28. In region 24, a coating contains antibody 24-1 bonded to enzyme 24-2. In region 26, antigen 26-1 is bonded to antibody 26-2, wherein antibody 26-2 is immobilized. Region 28 contains substrate 28-1.

Upon the addition of test solution containing antigen tested for, conjugate 24-1/24-2 is reconstituted whereby a conjugate is formed with the test antigen. The conjugate passes through region 26 to region 28, whereby enzyme 24-2 reacts with substrate 28-1 to indicate the presence of test antigen. In the absence of antigen in the test solution, a conjugate 24-1/24-2/26-1/26-2 is formed by the immunological coupling between antigen 26-1 and immobilized antibody 26-2 and mobile antibody 24-1. Thus, enzyme 24-2 does not reach substrate 28-1. As in FIG. 1, antibodies 24-1, 26-2 may be like or different, depending upon antigen 26-1.

In FIG. 3, a device of greater stability is formed by bonding glucose oxidase 32-1 to antibody 32-2 in region 32. Antibody 32-3 is bonded to peroxidase enzyme 32-4, as in FIG. 2. Antigen 34-1 is immobilized in region 34. Substrate 36-1, in region 36, contains glucose. Upon the addition of test solution containing antigen tested for, conjugates 32-1/32-2 and 32-3/32/4 each become bound to test antigen, whereby they pass to region 36. Glucose oxidase 32-1 reacts with glucose in region 36, in the presence of air, to produce hydrogen peroxide, a reagent in the indication reaction. In the absence of test antigen, antigen 34-1 traps conjugates 32-1/32-2, 32-3/32-4, whereby the absence of test antigen is indicated.

As can be seen in FIG. 4, the device of FIG. 1 has been modified to include the glucose oxidase/glucose reaction of FIG. 3.

Figure 5:
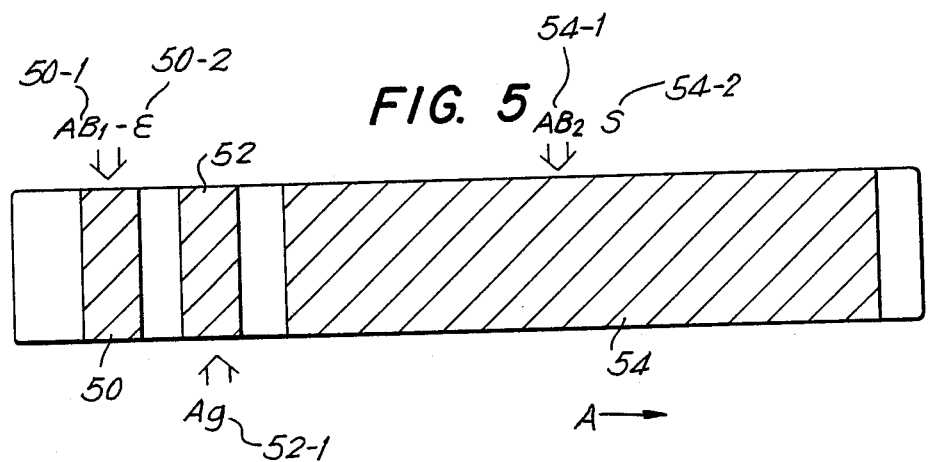

In FIG. 5, antibody 50-1 is bonded to enzyme 50-2, in region 50. Antigen 52-1 is immobilized in region 52. Region 54 contains immobilized antibody 54-1 and substrate 54-2. Upon the addition of test solution containing antigen tested for, competition arises for binding sites on antibody 50-1 between test antigen and antigen 52-1. Conjugate 50-1/50-2 passes to region 54 in the presence of test antigen. The distance along which indication occurs in region 54, in the direction A, provides information regarding the quantity of test antigen, as a result of conjugate formation between bound antibody 54-1 and conjugate 50-1/50-2. In the absence of test antigen, conjugate 50-1/50-2 becomes bonded and immobilized in region 52.

Figure 6:
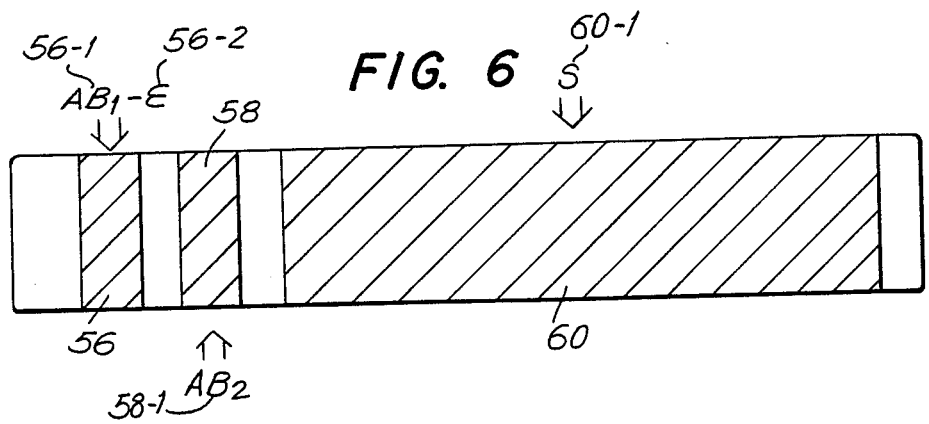

In the embodiment shown in FIG. 6, no antigen is required in the test device. Region 56 contains antibody 56-1 bound to enzyme 56-2. Region 58 contains immobilized antibody 58-1. In the presence of test antigen, a conjugate is formed between antibody 56-1, the test antigen, and antibody 58-1. Accordingly, enzyme 56-2 does not reach substrate 60-1, and color gradually disappears, in this case indicating the presence of test antigen. In the absence of test antigen, conjugate 56-1/56-2 is free to migrate to region 60, wherein the indication reaction occurs, and color remains, thus indicating absence of test antigen.

An advantage to the device 10 of the invention over the prior art is now readily apparent. In U.S. Pat. No. 4,446,232, for example, antigen 26 must be fairly pure. Particularly, there must be sufficient antigen in layer 14 to capture substantially all of the unconjugated antibody from layer 12. Obtaining pure antigen is expensive. The present invention avoids this limitation by employing antibodies in the selection of appropriate antigen. For example, monoclonal antibodies may be obtained by the hybridoma, chromatographic or affinity methods in high quantity at relatively low cost. The device antigen employed in the embodiments shown in FIGS. 1, 2 and 4 can be selected by the corresponding antibody. Accordingly, a higher degree of test antigen affinity may be obtained at low cost. As a result, the test is accurate and easily interpreted. In the embodiment shown in FIG. 6, no antigen is required, resulting in the greatest cost savings. For example, crude antigen sources, such as urine, may be used as a source of antigen, whereby selection is carried out by affinity.

The invention affords great flexibility in the selection of reagents. For example, the enzyme horseradish peroxidase (HRP) may be used, which reacts with a substrate comprising hydrogen peroxide ($H_2O_2$), the chromogen tetramethylbenzidine (TMB), and an appropriate stabilizer. (See copending, commonly assigned U.S. application Ser. No. 721,102, now abandoned). Other appropriate enzymes, such as alkaline phosphatase, and indicators may be used in accordance with the invention. In each embodiment, an antibody specific to the test antigen is bonded to the enzyme. Accordingly, the only reagent which must be of high purity is this antibody. As antigen specific antibodies can be inexpensively produced in great quantity at low cost, the invention provides a less expensive, higher accuracy assay device. The selection of antibodies depends upon the device and test antigens, for example, whether they are multideterminant or multiepitopic. Further, the antibodies should not cross-react with inappropriate antigen.

A further advantage to the invention is enhanced indication readability in all embodiments, and particularly for the embodiment shown in FIG. 5. Since antibody 54-1 is bound, color change, in the case of a chromogenic substrate, will be sharply defined, and indicative of the quantity of test antigen. In the prior art, enzyme diffuses throughout a substrate layer, whereupon a light color indicates a low test antigen concentration, and a darker color indicates a higher concentration. This obviously presents problems of accurate analysis, and typically requires color comparison with a reference chart. In accordance with the invention, all substrate molecules are progressively reacted due to immobilization through conjugation with antibody 54-1. For low test antigen, a short, but darkly colored band extends in the direction A in region 54. The higher the test antigen level, the longer the color band, however, the color density remains constant.

The assay devices of the invention are additionally more sensitive than the prior art. By preforming immunological bonds, only one valence on the antibody must become occupied by test antigen. Sensitivity is thus increased by orders of magnitude. This is particularly important where results are interpreted by non-skilled users.

Figure 7:
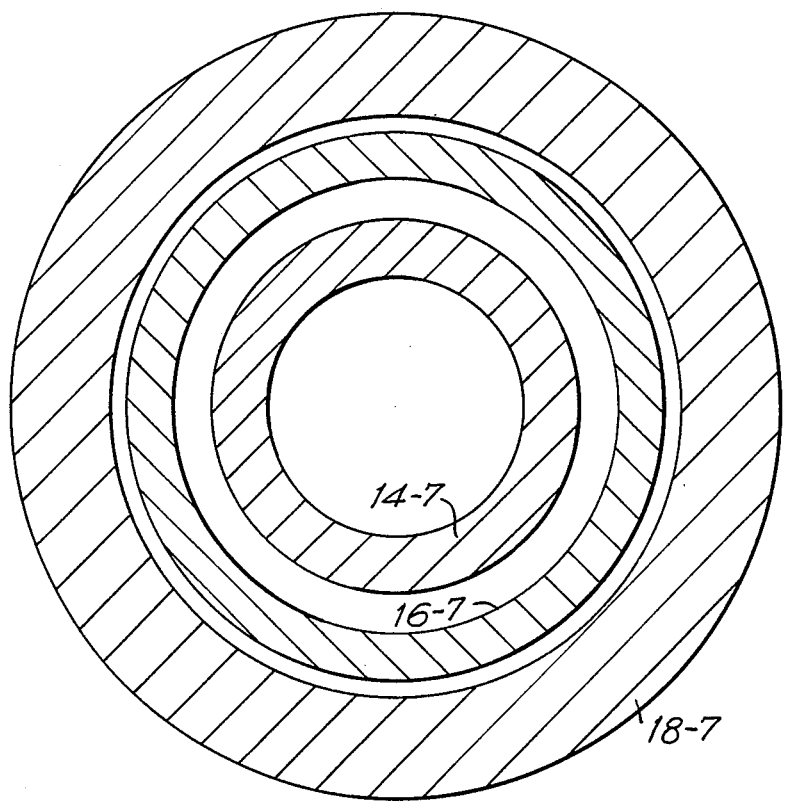
FIG. 7 is a schematic representation of an alternative assay configuration in accordance with the invention.

Device 10 may have other forms, such as the form shown in FIG. 7. Test solution is placed at the center of the disc. Rings 14-7, 16-7, and 18-7 correspond to FIG. 1, for example.

While various aspects of the invention have been set forth by the drawings and the specification, it is to be understood that the foregoing detailed description is for illustration only and that various changes in parts, as well as the substitution of equivalent constituents for those shown and described, may be made without departing from the spirit and scope of the invention as set forth in the appended claims.

What is claimed is:

1. An apparatus for indicating a test antigen in a solution, comprising:
   (a) a porous support having a plurality of regions;
   (b) a first antibody bound to an enzyme to form an enzyme-linked first antibody; said enzyme-linked first antibody being disposed within one of said regions;
   (c) a second antibody immobilized within a region other than that of the enzyme-linked first antibody; and
   (d) a substrate disposed in a region other than the region of said enzyme-linked first antibody, or the region of said second antibody, said substrate being capable of reacting with said enzyme to yield an indication of test antigen;
   said regions being disposed such that the solution flows through the region of said enzyme-linked first antibody to the region of said second antibody and then to the region of said substrate.

2. An apparatus for indicating a test antigen in a solution, comprising:
   (a) a porous support having a plurality of regions;
   (b) a first antibody bound to an enzyme to form an enzyme-linked first antibody; said enzyme-linked first antibody being disposed within one of said regions;
   (c) an antigen which will immunologically bind to said enzyme-linked first antibody, said antigen being disposed in a region other than the region of said enzyme-linked first antibody;
   (d) a second antibody immobilized within a region other than the region of said enzyme-linked first antibody, or the region of said antigen;
   (e) a substrate disposed in the region of said second antibody;
   said regions being disposed such that the solution flows through the region of said enzyme-linked first antibody to the region of said antigen, and then to the region of said second antibody and said substrate.

3. The apparatus of claim 1, wherein said first antibody is immunologically bound to an antigen and wherein said regions are disposed such that the solution flows through the region of said enzyme-linked first antibody bound to said antigen, to the region of said second antibody and then to the region of said substrate.

4. The apparatus of claim 3, wherein said enzyme bound to said first antibody bound to said antigen is glucose oxidase and glucose is present in said region of said substrate.

5. The apparatus of claim 3, wherein glucose oxidase is bound to said antigen which is immunologically bound to said first antibody and glucose is present in the region of said substrate.

6. The apparatus of claim 1, wherein said second antibody is immunologically bound to an antigen and wherein said regions are disposed such that the solution flows through the region of said enzyme-linked first antibody to the region of said second antibody bound to said antigen and then to the region of said substrate.

7. The apparatus of claim 1 or 2, wherein said regions are in the form of concentric circles.

8. The apparatus of claim 1 or 2, wherein said regions are in the form of consecutive transverse layers.

9. The apparatus of claim 1 or 2, wherein said regions are in the form of superimposed layers.

10. The apparatus of claim 1 or 2, wherein said substrate comprises tetramethylbenzidine.

11. The apparatus of claim 1 or 2, wherein said enzyme is horseradish peroxidase.

12. The apparatus of claim 1 or 2, wherein said enzyme is alkaline phosphatase.

13. An apparatus for indicating the presence of test antigen in a solution comprising:
   (a) a bibulous microporous support having a plurality of distinct regions;
   (b) a first antibody disposed within one of said regions, said antibody being bound to an enzyme to form an enzyme-linked first antibody;
   (c) a second antibody disposed within the same region as that of said enzyme-linked first antibody, said second antibody being bound to glucose oxidase;
   (d) an antigen which will immunologically bind to said enzyme-linked first antibody and to said second antibody, said antigen being immobilized in a region other than that of said enzyme-linked first antibody and that of said second antibody; and
   (e) a substrate comprising glucose, said substrate being in a region other than that of said enzyme-linked first antibody and said second antibody and that of said antigen, said substrate being capable of reacting with said glucose oxidase and said enzyme to yield an indication of test antigen;

said region being disposed such that said solution flows through the region of said enzyme-linked first antibody and the region of said second antibody, to the region of said antigen and then to the region of said substrate.

14. A method of determining the presence of an antigen in a test solution, comprising the steps of:
 (a) reacting the test solution with a first antibody bound to an enzyme and disposed on a porous support to form a first migrating solution comprising test solution and reconstituted first antibody bound to an enzyme;
 (b) reacting the first migrating solution of step (a) with a second antibody immobilized on said support to form a second migrating solution; and
 (c) reacting the second migrating solution of step (b) with a substrate capable of reacting with said enzyme and which is disposed on said support.

15. The method of claim 14, wherein an antigen is bound to the first antibody prior to the reaction of step (a).

16. The method of claim 15, wherein glucose oxidase is bound to said antigen bound to the first antibody prior to the reaction of step (a); and glucose is provided to the region of said substrate prior to the reaction of step (c).

17. The method of claim 14, wherein an antigen is bound to the second antibody prior to the reaction of step (b).

18. The method of claim 14, wherein the enzyme bound to said first antibody is glucose oxidase.

* * * * *